United States Patent [19]

Hendler

[11] Patent Number: 4,985,465

[45] Date of Patent: Jan. 15, 1991

[54] METHOD FOR INHIBITING VIRAL AND RETROVIRAL INFECTIONS

[76] Inventor: Sheldon S. Hendler, 2159 Avenida de la Playa, La Jolla, Calif. 92037

[21] Appl. No.: 381,132

[22] Filed: Jul. 14, 1989

[51] Int. Cl.$^5$ ...................... A01N 31/00; A61K 31/10
[52] U.S. Cl. .................................................... 514/712
[58] Field of Search .................... 252/45; 524/331; 514/712

[56] References Cited

U.S. PATENT DOCUMENTS

| | | | |
|---|---|---|---|
| 3,574,853 | 4/1971 | Barnhart | 424/337 |
| 3,576,883 | 4/1971 | Neuworth | 260/609 |
| 3,692,907 | 9/1972 | Fleming et al. | 424/248 |
| 3,862,332 | 1/1975 | Barnhart et al. | 424/337 |
| 4,350,707 | 9/1982 | Keith et al. | 424/346 |
| 4,560,799 | 12/1985 | Spivack et al. | 568/47 |
| 4,719,237 | 1/1988 | McCaughan | 514/712 |

OTHER PUBLICATIONS

Snipes, Wallace, CA 82:149903x, 1975.
Carew, Thomas, CA 18016125d, 1988.
DeMeglio et al., Chem. Abst. 104:28675p (1986).
Mordasini et al., Chem. Abst. 96:7912x (1982).
Ramos et al., Chem. Abst. 95:150171g (1981).
Hoshide et al., Chem. Abst. 93:149970u (1980).
Hoshide et al., Chem. Abst. 93:94980q (1980).
Hoshide et al., Chem. Abst. 93:71280x (1980).
Prous et al., Chem. Abst. 89:16371v (1978).
Kabara et al., Chem. Abst. 88:83965j (1978).
Kritchevsky et al., Chem. Abst. 74:123504c (1971).
Barnhart et al., Chem. Abst. 73:64643b (1970).
Drake et al., Chem. Abst. 72:20544v (1970).
Hendler, S., "The Complete Guide to Anti-Aging Nutrients", Simon and Schuster, New York, (1984).
Cupp et al., Antimicrobial Agents and Chemotherapy 8:698-706 (1975).
Brugh, Science 197:1291-1292 (1977).
Oda, et al., Science 244:974-976 (1989).
Hendler, S., "The Oxygen Breakthrough", William Morrow and Company, Inc., New York (1989).
Nara, et al., Aids Res. and Human Retroviruses 3:283-302 (1987) (May Ann Liebert, publ.).
Nara and Fischinger, Nature 332:469-470 (1988).
Maeda, H., Science News, 325, May 27 (1989).
Pirtle, E. C., et al. Am. J. Vet. Res. 47:1892-1895 (1986).
Kim, K. S. et al., J. Infec. Dis. 138:91-94 (1978).
Keith, A. D. et al., Proc. Soc. Exp. Biol. and Med. 170:237-244 (1982).
Freeman, D. J., et al., Clin. Pharmacol. Ther. 38:56-59 (1985).
Wanda, P. et al., Antimicrobial Agents and Chemotherapy 10:96-101 (1976).
Hammersatedt, R. H. et al., Biology of Reproduction 14:381-397 (1976).
Carew, T. E. et al., PNAS U.S.A. 84:7725-7729 (1987).

Primary Examiner—Douglas W. Robinson
Assistant Examiner—R. Travers
Attorney, Agent, or Firm—Knobbe, Martens, Olson & Bear

[57] ABSTRACT

This invention relates to a method for inhibiting viral and retroviral infections via the use of various compounds, including antioxidants, and compounds corresponding to the formula

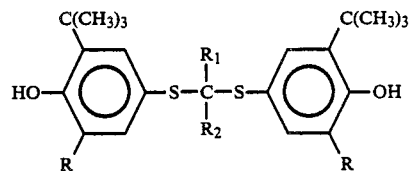

wherein R in each occurrence thereof independently represents lower alkyl of from one to four carbon atoms, inclusive, and wherein $R_1$ represents methyl and $R_2$ represents methyl or ethyl. This invention further discloses methods for inhibiting viral and retroviral infections using compounds including bis(3,5-di-tert-butyl-4-hydroxyphenyl) acetone mercaptole, bis(3,5-di-tert-butyl-4-hydroxyphenyl) butanone mercaptole, bis(3-tert-butyl-4-hydroxy-5-isopropylphenyl) acetone mercaptole, bis(3-tert-butyl-4-hydroxy-5-methylphenyl) acetone mercaptole, 4,4'-thiobis(6-tert-butyl-o-cresol), 1,3,5-trimethyl-2,4,6-tris(3,5-di-tert-butyl-4-hydroxybenzyl) benzene, 4,4'-methylenebis(2,6-di-tert-butylphenol), 2,6-di-tert-butyl-α-dimethylamino-p-cresol, and 4,4'-methylenebis(2,6-di-tert-butylphenol).

19 Claims, No Drawings

METHOD FOR INHIBITING VIRAL AND RETROVIRAL INFECTIONS

BACKGROUND OF THE INVENTION

There are urgent and compelling reasons for the development of more efficacious and safer treatments of viral and retroviral infections. It is estimated that at least one and a half million people in the United States alone have been infected with the human immunodeficiency (HIV) or AIDS virus. HIV causes a decay of a major arm of the immune system, the immune helper cells (T4 helper or CD4+ helper cells). This decay leads to a wide spectrum of diseases, generally called HIV disease, of which AIDS is the most serious and devastating form. It is anticipated that over one third of the budget for medical care in the U.S. will be consumed on HIV disease. There is an escalating incidence of other viral diseases as well. For example, cytomegalovirus (CMV) infection is rapidly increasing in the teenage population of the United States.

In recent years, many investigators have proposed novel treatments for combating insidious forms of disease, many involving viruses or retroviruses as the causative agents. Due to the many differences that separate these pathogens—including, for example, their structure, their method of replication and their susceptibility to or resistance to various treatment modalities—one might not expect a single method of inhibiting the development of viral and retroviral infections to be feasible. Nevertheless, such a methodology is now available, due to the unanticipated efficacy of known and novel compounds in affecting membrane fluidity, among other things.

In my practice and in my investigations, I nave noted that certain viruses and retroviruses including, for example, cytomegalovirus (CMV), herpes simplex virus, herpes zoster virus, Epstein-Barr virus (EBV), Newcastle Disease virus, Semliki Forest virus, influenza viruses, pseudorabies virus, and human immunodeficiency virus (HIV), are of the lipid membrane variety. I have also observed that certain ubiquitous preservatives, namely, butylated hydroxyanisole (BHA) and butylated hydroxytolulene (BHT), were reported in various sources as possessing some efficacy in treating various viral infections. (See Hendler, S., "The Complete Guide to Anti-Aging Nutrients," Simon and Schuster, New York, 1984.) For example, Cupp, et al., in *Antimicrobial Agents and Chemotherapy* 8: 698-706 (1975) reported that the lipid-containing bacteriophage PM2 could be inactivated by BHT. Similarly, Brugh reported that BHT was effective in protecting chickens exposed to Newcastle Disease virus, in *Science* 197: 1291-1292 (1977).

In addition, it has been theorized that free oxygen radicals may be involved in the pathogenesis of certain viral infections (see Oda, et al., *Science* 244: 974-976 (1989), and that antioxidants may have an impact upon viral or retroviral infections (see Hendler, S., "The Oxygen Breakthrough," William Morrow and Company, Inc., New York, 1989). These observations led me to investigate whether there might be substances possessing the ability to fluidize viral membranes, or otherwise affect their structures, in ways that make them less capable of infecting cells. The invention disclosed herein is not limited to or by a particular theory of operation, however.

Therefore, in response to this pervasive need for safer and more efficacious treatments of viral and retroviral infections, the present invention relates to a method for inhibiting such infections via use of known compounds with unexpected efficacy in combating viral and retroviral infections. The present invention also suggests the use of novel compounds to inhibit these infections, as well as methods for their use in living organisms.

SUMMARY OF THE INVENTION

Ideally, one type of substance that could conceivably affect the infectivity of a viral or retroviral agent should have some or all of the following characteristics: (a) solubility in lipid membranes, with preferential solubility in the lipid membranes of viruses as opposed to the cells of the body of the host; (b) ability to extract cholesterol from viral membranes; (c) antioxidant ability to prevent lipid peroxidation; (d) easy absorbability into the body; (e) the ability to penetrate the blood-brain barrier; and (f) a very high therapeutic-to-toxicity index. It is anticipated that all membraned viruses, including herpes simplex, herpes zoster, CMV, EBV, influenza viruses, and the human immunodeficiency viruses may be inhibited to some extent by such substances at doses that will not produce toxic side effects. The invention disclosed within is not limited to or by a particular theory of operation, however. It is simply suggested that the observed efficacy of compositions suggested by the present disclosure may be due, at least in part, to the characteristics noted above.

This invention relates to novel compositions and methods for using same for inhibiting viral and retroviral infections. In particular, the use of sterically hindered phenolic antioxidants is suggested. Even more particularly, the invention is directed to methods for using novel pharmaceutical compositions to inhibit viral and retroviral infections in vivo wherein the compositions comprise an effective amount of a bis(dialkylphenol) mercaptal or a bis(dialkylphenol) mercaptole compound.

One candidate substance which proved to have unexpectedly promising antiviral activity in this regard is the drug probucol, which is obtainable under the name Lorelco (Merrell Dow Pharmaceuticals, Inc.). Methods for utilizing this particular compound in lowering serum cholesterol are set forth in U.S. Pat. No. 3,862,332, which is incorporated herein by reference.

It is thus one object of this invention to suggest methods for using novel pharmaceutical compositions to inhibit viral and retroviral infections upon the administration of such compositions to living organisms. A further object of this invention is to provide a novel method for inhibiting viral and retroviral infections in living organisms. Another object of the present invention is to provide novel uses for existing compositions which have the ability to inhibit viral and retroviral infections in living organisms, and which have low toxicity at dosage levels consistent with their indicated activity. A further object of this invention is to suggest methods for the alleviation of viral and retroviral infections in a variety of organisms, including plants, animals, and more particularly, in humans.

One embodiment of the present invention discloses a method for inhibiting viral and retroviral infections in living organisms comprising administering to living organisms an effective amount of a compound corresponding to the formula

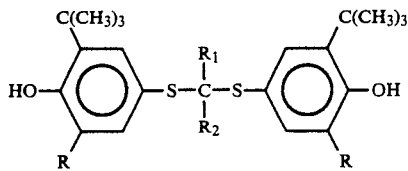

wherein R in each occurrence thereof independently represents lower alkyl of from one to four carbon atoms, inclusive, and wherein $R_1$ represents methyl and $R_2$ represents methyl or ethyl. In another embodiment, R represents tertiary butyl. In additional embodiments, the compound utilized may be bis(3,5-di-tert-butyl-4-hydroxyphenyl) acetone mercaptole, bis(3,5-di-tert-butyl-4-hydroxyphenyl) butanone mercaptole, bis(3-tert-butyl-4-hydroxy-5-isopropylphenyl) acetone mercaptole, or bis(3-tert-butyl-4-hydroxy-5-methylphenyl) acetone mercaptole.

The present embodiment additionally discloses a method for inhibiting viral and retroviral infections in living organisms comprising administering to a living organism an effective amount of an antioxidant compound. In one embodiment of the present invention, the antioxidant compound may also be sterically hindered; in another preferred embodiment, the compound is also phenolic. Examples of such preferred antioxidants include 4,4'-thiobis(6-tert-butyl-o-cresol), 1,3,5-trimethyl-2,4,6-tris(3,5-di-tert-butyl-4-hydroxybenzyl) benzene, 4,4'-methylenebis(2,6-di-tert-butylphenol), 2,6-di-tert-butyl-α-dimethylamino-p-cresol, or 4,4'-methylenebis(2,6-di-tert-butylphenol).

In one preferred embodiment, the compounds disclosed herein are incorporated in a pharmaceutically acceptable carrier or excipient. Preferred methods of administering the compounds of the present invention include parenteral, oral, intraperitoneal, transdermal and topical administration, as well as administration via inhalation.

DETAILED DESCRIPTION

It has been observed that the membrane fluidity or other properties of viral and retroviral agents may be disturbed and affected by administration of sterically hindered phenolic antioxidants, such compounds corresponding to derivatives of butylated hydroxytoluene (BHT), said derivatives comprising conjugates of from about one to four modified BHT moieties. Examples of such compounds, which may collectively be referred to herein as "antioxidants", include the following Ethanox ® compounds, which are commercially available from Ethyl Corporation (Baton Rouge, La.): 4,4'-thiobis(6-tert-butyl-o-cresol) ("Ethanox ® 322"); 4,4'-methylenebis(2,6-di-tert-butylphenol) ("Ethanox ® 702"); 2,6-di-tert-butyl-α-dimethylamino-p-cresol ("Ethanox ® 703"); 1,3,5-trimethyl-2,4,6-tris(3,5-di-tert-butyl-4-hydroxybenzyl) benzene ("Ethanox ® 330"); and about 80 wt % methylene bridged poly alkly phenols, over 50% of which comprises 4,4'-methylenebis(2,6-di-tert-butylphenol), about 5 wt % solvents, and about 15 wt % alkylated phenols, principally 2,4,6 tri-tert-butylphenol ("Ethanox ® 728"). (Ethanox ® is a registered trademark of Ethyl Corporation.)

The membrane fluidity or other properties of viral and retroviral agents may also be disturbed via administration of a substituted compound, or a composition or dosage unit form, being an S,S'-di-substituted mercaptal of an aldehyde or an S,S'-di-substituted mercaptole of a ketone containing from two to twenty carbon atoms, inclusive, wherein the substituents are 3-tertiary-alkyl-4-hydroxy-5-lower alkyl phenyl groups in which the tertiary alkyl groups are tertiary butyl groups and the lower alkyl groups are methyl, ethyl, propyl or butyl, such compounds corresponding to the following formula:

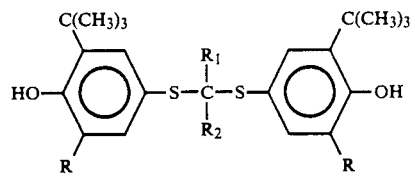

In the present specification and claims, R in each occurrence thereof independently represents lower alkyl of one, two, three, or four carbon atoms, inclusive; $R_1$ represents hydrogen or methyl, and $R_2$ represents methyl, ethyl, propyl, isobutyl, or linear alkyl, up to 20 carbon atoms. It is generally preferred to employ a compound wherein R, in both occurrences thereof, represents the same lower alkyl moiety of from one to four carbon atoms, inclusive. Another preferred group of compounds are those wherein $R_2$ represents methyl, ethyl, normal propyl, isobutyl, or linear alkyl. A particularly preferred group of compounds for use in the practice of the invention comprises the bis(3-tert-butyl-4-hydroxy-5-lower alkylphenyl) ketone mercaptoles corresponding to the above formula wherein $R_1$ is methyl, such compounds wherein R in each occurrence thereof represents the same lower alkyl moiety being also preferred. Another preferred group of compounds are those corresponding to the above formula wherein R, in each occurrence thereof, represents the same lower alkyl moiety selected from the group consisting of methyl, ethyl, isopropyl, and tertiary butyl and wherein $R_1$ represents methyl and $R_2$ represents methyl. Another preferred group comprises the bis(3,5-di-tert-butyl-4-hydroxyphenyl) ketone mercaptole compounds of the above formula, the compound bis(3,5-di-tert-butyl-4-hydroxyphenyl) acetone mercaptole being particularly preferred for use in the composition and method of the invention. These compounds can be prepared as disclosed in U.S. Pat. No. 3,862,332. For the sake of convenience, compounds having the above-described chemical structures will be referred to hereinafter as "substituted ketone mercaptole" compounds. It is to be understood that these compounds also function as antioxidants.

The above-referenced compounds can be administered topically, orally or parenterally by subcutaneous, intramuscular, intravenous or intraperitoneal injection or by implantation or the like, oral administration being preferred. The antioxidant compounds, including substituted ketone mercaptole compounds, are preferably administered as pharmaceutical compositions in dosage unit form. Such compositions can be prepared by known techniques, for example, tableting or encapsulation. The dosage units of the antioxidants, including the substituted mercaptole compounds, preferably contain from about 100 to about 200 to about 500 milligrams (mg) to about one to about five grams of the active ingredient. Dosage units, adapted for oral administration, such as tablets, capsules, lozenges, and the like, may contain up to about five grams of active ingredient, albeit they preferably contain from about 100 to about 500 mg of the active ingredient, for ease of administration. The compounds can also be administered as compositions adapted to be fed as part or all of the organism's diet.

In forming the compositions of the present invention, the active compound is incorporated in a pharmaceutical carrier. In the present specification and claims, the term "pharmaceutical carrier" refers to pharmaceutical excipients and includes nutritive compositions such as solid or liquid foodstuff. In the present specification and claims, "pharmaceutical excipient" refers to known pharmaceutical excipients which are substantially non-toxic and non-sensitizing at dosages consistent with their desired activity, e.g., with cholesterol reducing activity, in the case of probucol. A preferred pharmaceutical carrier is, for example, a surface-active dispersing agent.

Suitable solid pharmaceutical carriers which can be employed for formulating the compositions of the invention include starch, lactose, glucose, sucrose, gelatin, microcrystalline cellulose, powdered licorice, powdered tragacanth, malt, rice flour, silica gel, magnesium stearate, magnesium carbonate, hydroxypropyl methyl cellulose, chalk and the like, and compatible mixtures thereof. In the preparation of solid compositions, the active ingredient can be triturated with a solid pharmaceutical carrier or mixtures thereof, or otherwise mechanically milled to obtain a uniform mixture. The mixtures can be compressed into tablets or filled into capsules by known procedures, or they can be employed as powders or the like. The solid compositions generally contain from about 0.02 to about 90 percent by weight, inclusive, of the active ingredient, although neat dosages are also contemplated.

Among the liquid pharmaceutical carriers which can be utilized are ethyl alcohol, propylene glycol, polyethylene glycols, peanut oil, corn oil, water, saline solution, liposomes, glycerides, glycerine and water mixtures, glucose syrup, syrup of acacia, mucilage of tragacanth and the like, and compatible mixtures thereof.

The compounds of the present invention may be administered in various efficacious amounts. The preferred dosage range of active ingredient is from about 0.25 grams (gm) to about 5 gm per day, with a range of 0.5 gm to 2 gm per day being somewhat more preferable. The active ingredient may be administered topically, transdermally, orally, parenterally (e.g., subcutaneously, intravenously or intramuscularly), intraperitoneally, or via inhalation.

The invention can be better understood by way of the following examples which are representative of the preferred embodiments thereof, but which are not to be construed as limiting the scope of the invention.

EXAMPLE I

In vitro Inhibition Tests

The following compounds were tested for their ability to inhibit HIV-1 virus infection in vitro. The compounds tested were: (1) probucol (2.5%): (2) 2,6 dicyclopentyl phenol (5%); 2,6 dicyclohexyl p-cresol (5%); 3) 4,4'-thiobis(6-tert-butyl-o-cresol) ("Ethanox ® 332", 5%); (4) 4,4'-methylenebis(2,6-di-tert-butylphenol) ("Ethanox ® 702", 1.25%); (5) 2,6-di-tert-butyl-α-dimethylamino-p-cresol ("Ethanox ® 703", 5%); (6) 1,3,5-trimethyl-2,4,6-tris(3,5-di-tert-butyl-4-hydroxybenzyl) 1.25%): and 7) 4,4'-methylenebis(2,6-di-tert-butylphenol) benzene ("Ethanox ® 330", 1.25%); and (7) 4,4'-methylenebis(2,6-di-tert-butylphenol) ("Ethanox ® 728", (5%).

The compounds were diluted at 300, 200, 100, 30, 10, 3, and 1 microgram per milliliter (1µg/ml) in Complete RPMI 1640 media (Gibco Laboratories, Grand Island, N.Y.). The compound dilutions were pre-incubated with an HIV-1 (10 3.6 titer) diluted at 1:100 and 1:1000 for one hour and then plated onto a CEM-SS infectivity assay. (See Nara, et al., *Aids Res. and Human Retroviruses* 3: 283–302 (1987), Mary Ann Liebert, publ., or Nara and Fischinger, *Nature* 332: 469–470 (1988)). The dilutions were also pre-incubated onto the cells for one hour, then inoculated with 1:100 and 1:1000 dilutions of the HIV-1(10 3.6 titer) that contained no compound. Inoculum was aspirated off the wells after one hour and the cells were maintained for five days with compound and media, then read for plaques.

Of the above-listed compounds, probucol displayed the most significant effects upon HIV-1 plaque formation. It was specifically observed that probucol significantly inhibited plaque formation at concentrations of about 200 µg/ml under both test conditions—i.e., when pre-incubated with the HIV and when pre-incubated with the cells, without significant toxicity to the cells. Probucol also appeared to inhibit plaque formation at concentrations of about 100 µg/ml, albeit the inhibition was not as marked as at twice the concentration. Again, there was no significant toxicity to the cells. The effects of the Ethanox ® compounds tested were, in most cases, not always as marked as were those of probucol. Nevertheless, these phenolic antioxidants, and in particular, Ethanox ® 728, demonstrated efficacy as antiviral and antiretroviral agents.

EXAMPLE II

Clinical Tests

Probucol was administered to 5 adult male documented HIV-positive (HIV+) patients, ranging in age from 31–44 years at the time of diagnosis, in dosages consistent with those prescribed for treatment of hypercholesterolemia. All patients receiving probucol took 1 gram per day in divided doses for individually-varying lengths of time, as indicated below. Each patient was examined regularly and clinical observations were made and recorded by the same treating physician each time, except where indicated otherwise. Samples of each patient's blood were collected periodically and were tested for levels of T helper cells (CD4+ or T4) and T suppressor cells (CD8+ or T8). The CD4+:CD8+ ratio ("R") was also calculated each time. Blood samples taken prior to the initiation of probucol treatment were analyzed and compared with the samples taken during the treatment phase. The same parameters were tested in all samples. The results of this testing are set out below:

| Patient | Date | Clin. Observations | Test Results |
|---------|------|--------------------|--------------|
| A | 5/6/88 | HIV+ (determined 2/26/88); asymptomatic. | T4 - 532<br>T8 - 1427<br>R - 0.37 |
|   | 5/7/88 | 1 g/day probucol begun, in divided doses. | |
|   | 11/16/88 | Asymptomatic. | T4 - 1111<br>T8 - 1910<br>R - 0.58 |
|   | 5/5/89 | Asymptomatic. | T4 - 1161<br>T8 - 1879 |

-continued

| Patient | Date | Clin. Observations | Test Results |
|---|---|---|---|
| | | | R - 0.62 |
| B | 12/30/87 | AIDS with Kaposi's sarcoma. Received treatment with AZT prior to this time. AZT treatment was discontinued when patient became ill and developed a significant anemia. | T4 - 146<br>T8 - 393<br>R - 0.37 |
| | 12/31/87 | 1 g/day probucol begun, in divided doses. | |
| | 4/8/88 | Kaposi's lesions smaller. | T4 - 263<br>T8 - 867<br>R - 0.30 |
| | 12/1/88 | Lesions smaller and fewer in number. | T4 - 344<br>T8 - 847<br>R - 0.41 |
| | 3/10/89 | Smaller lesions, and fewer in number. | T4 - 347<br>T8 - 583<br>R - 0.60 |
| C | 12/9/87 | ARC (AIDS-related complex): thrush, eczema and lymphadenopathy | T4 - 601<br>T8 - 978<br>R - 0.61 |
| | 6/6/88 | Same as above | T4 - 533<br>T8 - 866<br>R - 0.62 |
| | 6/7/88 | 1 g/day probucol begun, in divided doses. | |
| | 8/12/88 | Clinical symptoms improved. | T4 - 654<br>T8 - 515<br>R - 1.27 |
| D | 4/14/87 | Fatigue and rash* | T4 - 530<br>T8 - 2000<br>R - 0.30 |
| | 6/30/87 | HIV+ (first documented)* | |
| | 7/1/87 | Increasing fatigue, rash and lymph node swelling* | T4 - 380<br>T8 - 1260<br>R - 0.30 |
| | 10/28/87 | ARC: symptoms of thrush, eczema, and generalized lymphadenopathy.* | T4 - 247<br>T8 - 845<br>R - 0.30 |
| | 11/5/87 | 1 g/day probucol begun, in divided doses. | |
| | 12/1/87 | Symptoms improved. | T4 - 457<br>T8 - 1828<br>R - 0.25 |
| | 2/2/88 | Symptoms resolved. | T4 - 520<br>T8 - 1751<br>R - 0.30 |
| | 6/7/88 | Symptom-free. | T4 - 512<br>T8 - 1536<br>R - 0.33 |
| E | 3/19/87 | HIV+; Asymptomatic.* | T4 - 710*<br>T8 - 1450*<br>R - 0.50* |
| | 7/14/87 | Asymptomatic.* | T4 - 560*<br>T8 - 1230*<br>R - 0.50* |
| | 2/3/88 | Asymptomatic.* | T4 - 520*<br>T8 - 1102*<br>R - 0.47* |
| | 4/27/88 | 1 g/day probucol begun, in divided doses. | |
| | 8/17/88 | Asymptomatic. | T4 - 679<br>T8 - 1462<br>R - 0.46 |

\* = Information reported by prior treating physician.

Although the invention has been described in the context of particular embodiments, it is intended that the scope of coverage of the patent not be limited to those particular embodiments, but be determined by reference to the following claims.

I claim:

1. A method of treating viral and retroviral infections in a mammal comprising administering to said mammal an effective amount of an antioxidant of the formula:

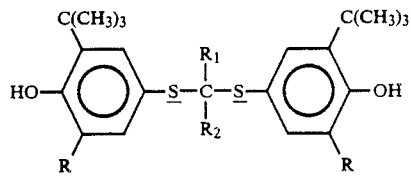

wherein R in each occurrence thereof independently represents lower alkyl of from one to four carbon atoms, inclusive: $R_1$ represents hydrogen or methyl; and $R_2$ represents methyl, ethyl, propyl, isobutyl, or linear alkyl, up to 20 carbon atoms.

2. The method of claim 1, wherein R represents tertiary butyl.

3. The method of claim 2 wherein said compound is bis(3,5-di-tert-butyl-4-hydroxyphenyl) acetone mercaptole.

4. The method of claim 2 wherein said compound is bis(3,5-di-tert-butyl-4-hydroxyphenyl) butanone mercaptole.

5. The method of claim 2 wherein said compound is bis(3-tert-butyl-4-hydroxy-5-isopropylphenyl) acetone mercaptole.

6. The method of claim 2 wherein said compound is bis(3-tert-butyl-4-hydroxy-5-methylphenyl) acetone mercaptole.

7. The method of claim 1, wherein said compound is sterically hindered by one or more bulky substituents in the immediate vicinity of the phenolic hydroxyl group.

8. The method of claim 7, wherein said compound is phenolic.

9. The method of claim 1, wherein said compound is 4,4'-thiobis(6-tert-butyl-o-cresol).

10. The method of claim 1, wherein said compound is 1,3,5-trimethyl-2,4,6-tris(3,5-di-tert-butyl-4-hydroxybenzyl) benzene.

11. The method of claim 1, wherein said compound is 4,4'-methylenebis(2,6-di-tert-butylphenol).

12. The method of claim 1, wherein said compound is 2,6-di-tert-butyl-α-dimethylamino-p-cresol.

13. The method of claim 1, wherein said compound comprises at least 40 wt % 4,4'-methylenebis(2,6-di-tert-butylphenol), less than about 41 wt % other methylene bridged poly alkyl phenols, 0–15 wt % 2,4,6 tri-tert-butylphenol, and about 5 wt % solvents.

14. The method of any one of claims 1 or 2, wherein said compound is incorporated in a pharmaceutically acceptable carrier or excipient.

15. The method of claim 14, wherein said compound is administered parenterally.

16. The method of claim 14, wherein said compound is administered orally.

17. The method of claim 14, wherein said compound is administered intraperitoneally.

18. The method of claim 14, wherein said compound is administered topically or transdermally.

19. The method of claim 14, wherein said compound is administered via inhalation.

* * * * *